US006233475B1

(12) United States Patent
Kim et al.

(10) Patent No.: US 6,233,475 B1
(45) Date of Patent: May 15, 2001

(54) METHOD FOR COORDINATING MR ANGIOGRAPHY SCAN WITH ARRIVAL OF BOLUS AT IMAGING SITE

(75) Inventors: Jae K. Kim; Richard I. Farb; Graham A. Wright, all of Toronto (CA)

(73) Assignee: Synnybrook Health Science Center, Toronto (CA)

( * ) Notice: Subject to any disclaimer, the term of this patent is extended or adjusted under 35 U.S.C. 154(b) by 0 days.

(21) Appl. No.: 09/156,884

(22) Filed: Sep. 18, 1998

(51) Int. Cl.$^7$ .................................................. A61B 5/05
(52) U.S. Cl. .............................................. 600/420; 324/309
(58) Field of Search ..................................... 600/420, 410, 600/419; 324/309, 307, 306; 424/9.3, 9.36

(56) References Cited

U.S. PATENT DOCUMENTS

| | | | |
|---|---|---|---|
| 5,588,431 | * 12/1996 | Mani et al. | 128/653.3 |
| 5,590,654 | * 1/1997 | Prince | 128/653.4 |
| 5,671,742 | * 9/1997 | Dumoulin et al. | 128/653.3 |
| 5,713,358 | * 2/1998 | Mistretta et al. | 128/653.2 |
| 5,799,649 | * 9/1998 | Prince | 128/653.4 |
| 5,842,989 | * 12/1998 | Zur | 600/410 |
| 5,924,987 | * 7/1999 | Mistretta et al. | 128/653.2 |
| 6,043,655 | * 3/2000 | Makita et al. | 324/309 |

* cited by examiner

Primary Examiner—Marvin M. Lateef
Assistant Examiner—Eleni Mantis Mercader
(74) Attorney, Agent, or Firm—Jenkens & Gilchrist, P.C.

(57) ABSTRACT

An MRI method is provided for determining the arrival of selected contrast material at a target artery or other fluid-carrying vessel after injection of contrast material at a remote vascular site. By precisely knowing the arrival time, an additional MR angiography scan of the artery may be readily coordinated with the onset of artery enhancement. Initiation of this MR angiography scan may be immediate. Alternatively, determination of the arrival time of a test bolus of contrast to the imaging site can be used to calculate the transit time of a test bolus from the injection site to the imaging site. This information may then be used as an estimate of a subsequent MR angiography scan using a full bolus of contrast. The method for determining contrast arrival includes injecting the contrast material at an injection site, and simultaneously commencing acquisition of a succession of MR images of a section taken through the target vessel, proximate to the imaging site. A succession of RF excitation pulses are applied to first and second zones to selectively saturate MR signals passing therethrough, the first and second saturation zones being positioned on opposing sides of the imaging section and respectively extending away therefrom, in opposite directions, along the vessel. Each MR image can be monitored, upon being acquired, to determine the arrival of the contrast material at the imaging site.

25 Claims, 5 Drawing Sheets

METHOD FOR COORDINATING MR ANGIOGRAPHY SCAN WITH ARRIVAL OF BOLUS AT IMAGING SITE

BACKGROUND OF THE INVENTION

The invention disclosed and claimed herein generally pertains to magnetic resonance (MR) angiography, i.e., to MR imaging of an artery or like vessel carrying blood or other fluid. More particularly, the invention pertains to a method of the above type wherein an amount of contrast agent, or bolus, is inserted into the vessel to enhance contrast between blood flowing through the vessel, and adjacent stationary tissue or other structure. Even more particularly, the invention pertains to a method of the above type for closely determining the arrival time of the bolus at a site or location of imaging.

It is now a well known practice in MR angiography to insert a volume of contrast agent, such as gadolinium chelate, into blood flowing along a vessel. The volume or mass of contrast agent is referred to as a bolus, and has the effect of shortening the T1 time of the blood. Thus, an MR image of the blood, acquired by a fast gradient echo or like technique, will show up very well with respect to adjacent stationary tissue of the vessel structure. These agents have been found to be very effective, particularly when used with three-dimensional (3D) MR angiographic techniques. However, if imaging occurs some minutes after the administration of contrast material, complex images are created in which distinction between target vessels (usually arterial) and other vasculature is difficult. Time-dependent leakage of contrast material into adjacent tissue increases background signal intensity, which adds a further hindrance to image interpretation. At present, there is increasing interest in imaging arteries by trying to capture first-pass arterial enhancements, resulting from use of contrast material, by coordinating the onset of a 3D MR angiographic sequence with injection of the contrast material. This approach is often referred to as "dynamic contrast material-enhanced 3D MR angiography", and aims at imaging arteries during first-pass arterial enhancement, prior to the onset of venous enhancement. Arteries targeted with this approach include the descending aorta and the mesenteric, renal, and hepatic arteries.

There are several basic approaches to capturing first-pass arterial enhancement. In the fixed transit time approach, imaging is initiated after a fixed time interval after injection. In the test bolus approach, a small test bolus of contrast is used to determine a priori the transit time of contrast from the time of injection at the injection site to the time of arrival at the imaging site. This information is then used to coordinate the initiation of a 3D MR angiographic sequence after the subsequent injection of a full bolus of contrast. In the automated trigger approach, only a full bolus of contrast is injected, and after detection of its arrival at the imaging site, a 3D MR angiographic sequence is initiated. In the latter two approaches, a method of determining the arrival of contrast at the imaging site is required.

While many studies use the fixed transit time approach, the true transit time of contrast material can vary on the order of tens of seconds from patient to patient, depending on each patient's cardiovascular status. For instance, typical transit times to the liver have been found to vary from 8 to 32 seconds. Even more important, the time window between the onsets of arterial and venous enhancement is usually just seconds in duration, and is therefore shorter than the imaging time in a typical 3D MR angiographic sequence. In the case of the liver, this time window has been noted to be as short as 8 seconds and to average approximately 16 seconds. Data collection from lower order k-space needs to occur during this time window, in order for final images to demonstrate only arterial enhancement. The shorter the time window, the more likely it becomes that the use of a fixed time delay will lead to suboptimal images that miss first-pass arterial enhancement prior to venous enhancement, and the greater the necessity for an accurate estimate of the transit time.

In applying dynamic contrast-enhanced 3D MR angiography to the carotid arteries, two important features have been noted. First, there is a very short optimal time window for imaging, typically 5–10 seconds, during which contrast material is within the arteries and the cranial circuit but has not yet reached the veins of the neck. Second, the blood-brain barrier prevents absorption of gadolinium-based contrast material, which creates a particularly strong venous signal during venous enhancement that complicates assessment of the arteries. For these two reasons, it is essential in dynamic contrast-enhanced 3D MR angiography of the carotid arteries to have accurate measurement or estimation of the patient-dependent transit time of contrast material, from injection site to imaging site.

SUMMARY OF THE INVENTION

The invention is generally directed to a method for determining the arrival time of selected contrast material along an artery or other vessel, between an injection site and a site of MR imaging. The method includes injecting the contrast material into blood or other fluid flowing through the vessel at the injection site. Coincident in time with injection of the contrast material, acquisition of a succession of MR images commences, each image being directed to the same section taken through the vessel, proximate to the imaging site. Excitation pulses are applied to first and second zones to selectively saturate MR signals passing therethrough, the first and second saturation zones being positioned on opposing sides of the imaging section, and respectively extending along the vessel. The MR images are monitored as they are respectively acquired, to detect the first of such images to indicate arrival of the contrast material at the imaging site.

In a preferred embodiment of the invention, each of the MR images is acquired during a brief time period, such as a period of approximately 1 second, by means of a fast sequence such as a two-dimensional gradient recalled echo sequence. The imaging section comprises a section taken through the vessel which is oriented in substantially perpendicular relationship to the direction of fluid flow. Each of the saturation zones is in abutting relationship with the section, and the excitation pulses applied to the saturation zones comprise RF pulses of selectively low flip angle, such as 18°. A series of pulses, such as five, produces a steady state MR environment in the saturation zones.

In a useful embodiment, the vessel comprises a carotid artery, and the injection site is at a venous site in the antecubital fossa. In this embodiment, a test bolus of contrast is employed to determine transit time as described above. Thereafter, a full bolus, comprising a dose of contrast material having a substantially greater volume than the test bolus, is injected into the vessel. After a delay time equal to the transit time, following full bolus injection, a 3D MR angiography scan is commenced at the imaging site. If the time window for imaging is very short, centric view ordering is usefully employed, to ensure collection of as much lower order k-space data as possible.

In another useful embodiment, that of an automated trigger examination, using a similar intravenous set-up, the contrast material comprises a full bolus, and after detection at the imaging site, a 3D MR angiography scan is immediately commenced at the imaging site. Again, if the time window for imaging is very short, centric view ordering is usefully employed.

In view of the above, important purposes of the invention include providing a method for more effectively coordinating commencement of a 3D MR angiographic sequence with injection of contrast material into an associated artery or vessel, and capturing first-pass arterial contrast enhancement, i.e., imaging when a contrast material first arrives at the imaging site, and prior to the onset of venous enhancement. Other purposes include determining transit time of a bolus between an injection site and an imaging site with substantial accuracy and precision, for individual patients, and minimizing sensitivity to pulsatile flow enhancement by providing saturation zones on either side of the section from which images are acquired. Further purposes and advantages of the invention will become more readily apparent from the following description, taken together with the accompanying drawings.

DETAILED DESCRIPTION OF THE PREFERRED EMBODIMENT

Figure 1:
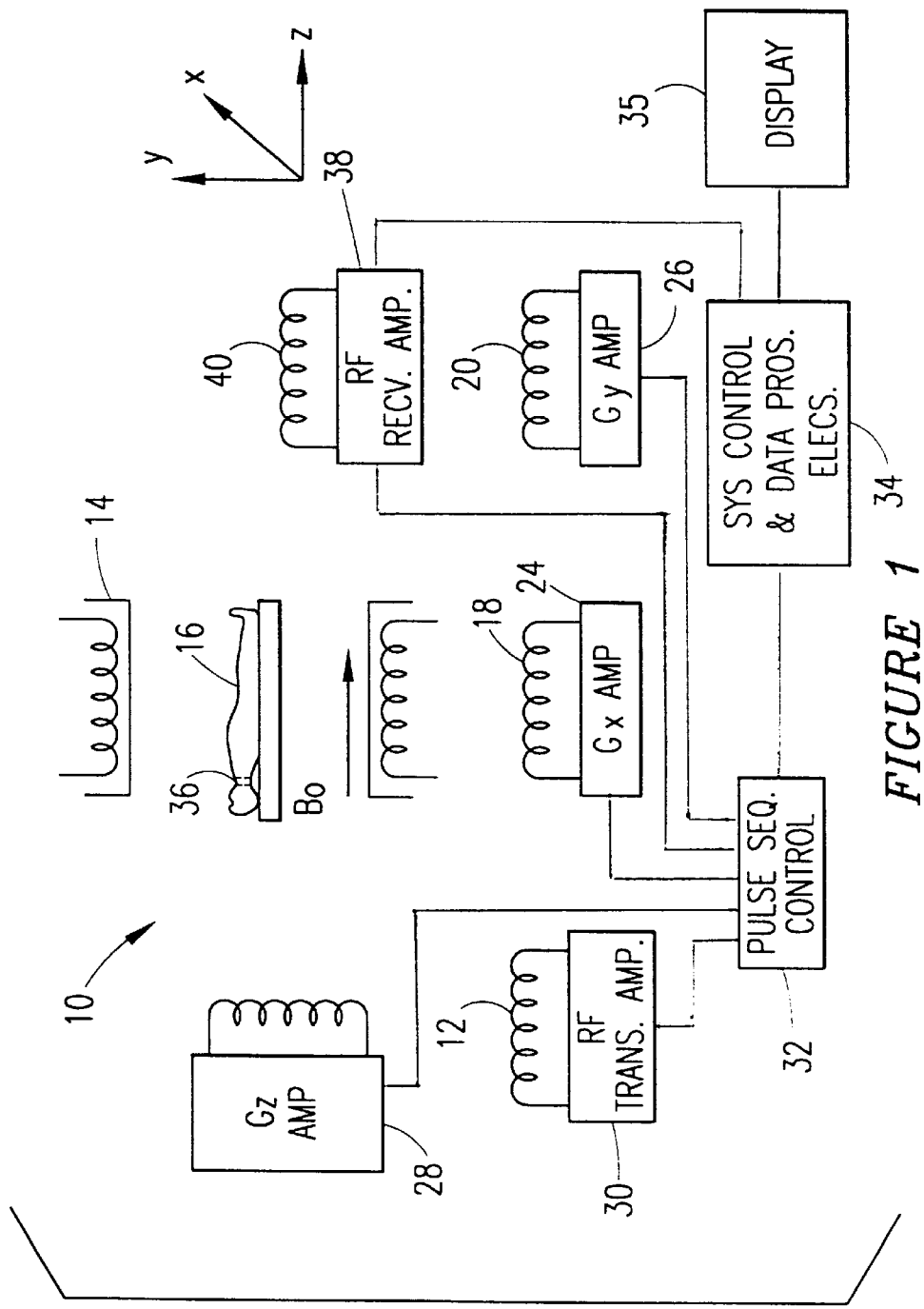
FIG. 1 is a schematic diagram showing basic components of an MR system for use in practicing embodiments of the invention.

Referring to FIG. 1, there are shown the basic components of an MR system or scanner 10 which may be operated to acquire MR data in accordance with the invention described herein. System 10 includes an RF transmit coil 12, as well as a cylindrical magnet 14 for generating a main or static magnetic field Bo in the bore thereof. RF coil 12 is operated to transmit RF excitation signals into a patient or other subject of imaging 16 supported in the magnet bore, in order to produce MR signals. For example, excitation signals may be directed to the neck region 36 of patient 16, as part of a procedure for imaging carotid arteries. System 10 further includes gradient coils 18, 20 and 22 for generating Gx, Gy, and Gz magnetic field gradients relative to orthogonal X-, Y- and Z-reference axes, respectively. FIG. 1 shows each of the gradient coils 18, 20 and 22 respectively driven by gradient amplifiers 24, 26 and 28, and RF coil 12 driven by transmit amplifier 30. FIG. 1 further shows an RF coil 40, which is operated in association with a receive amplifier 38 to acquire MR signals from subject 16. In some arrangements, coil 40 and coil 12 comprise the same RF coil, which is operated in alternate modes during the imaging sequence. However, to image neck region 36, coil 40 usefully comprises a standard receive-only neck coil. System 10 is further provided with a pulse sequence control 32, which is operated to control the RF and gradient amplifiers, and to thereby generate pulse sequences to produce and acquire sets of MR signals. System 10 also includes system control and data processing electronics 34, for operating respective components of system 10 to acquire MR data, in accordance with the invention, and to construct images thereof. System 10 may be further provided with a display screen 35 or the like for displaying images. The construction, functions, and interrelationships of components of MR system 10 are well known and described in the prior art, such as in U.S. Pat. No. 5,672,969, issued Sep. 30, 1997 to Zhou et al.

Figure 2:
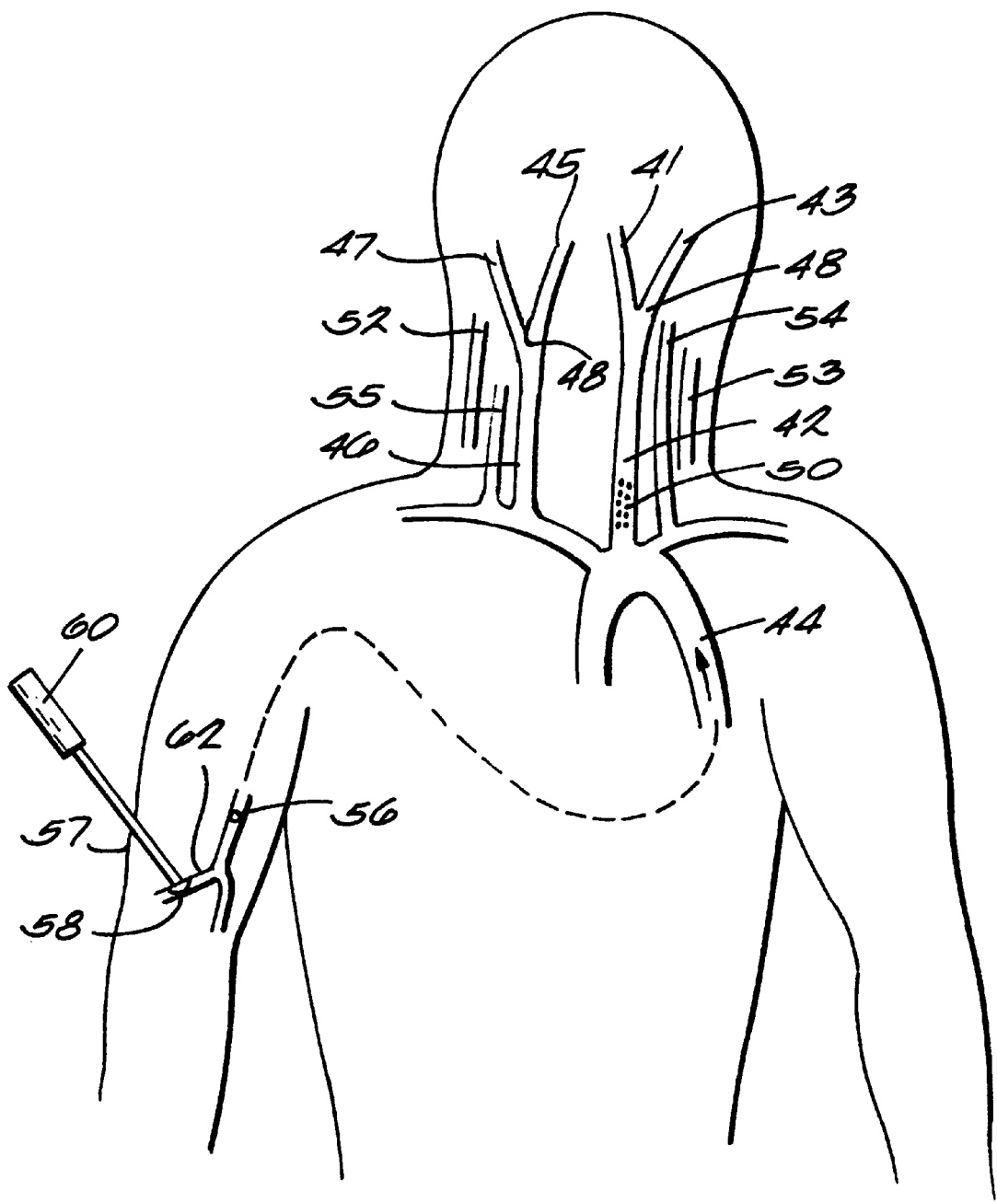
FIG. 2 is a perspective view showing selected arteries and veins of a subject of MR angiography.

Referring to FIG. 2, there is shown an aortic artery 44 of patient 16, which eventually branches into left and right common carotid arteries 42 and 46, respectively, in the neck. These arteries both give rise to their respective internal and external carotid artery branches 41 and 43, and 45 and 47, respectively, after a bifurcation 48 in the upper portion of the neck. Blood 50 flows upward into the brain through the carotid arteries, and returns through neck veins such as right internal jugular vein 52. As is well known, stenosis in the internal carotid arteries, which increases the risk of stroke thereof, is a serious concern. In applying MR angiography to the assessment of carotid artery stenosis, it has been recognized that contrast agents may be usefully employed for arterial enhancement. However, after the contrast agent has arrived at the carotid arteries, there is only a brief optimal period, typically less than ten seconds, before the contrast agent returns through vein 52 or the like. Thereupon, the veins as well as the target arteries are enhanced, resulting in complex MR images in which distinction between target arteries and other vasculature is difficult. FIG. 2 further shows left and right vertebral arteries 54 and 55, and left internal jugular vein 53. It would clearly be desirable to acquire as much MR data of the target arteries as possible, during the above optimal period. To maximize such data acquisition, the transit time of the contrast material, from the injection site thereof to the location of the target arteries, must be precisely known, for each individual patient.

Referring further to FIG. 2, there is shown contrast material, comprising a test bolus 56, inserted into a vein of an arm 57 of patient 16, to determine bolus transit time. More specifically, test bolus 56 is injected into the blood stream at a selected injection site 58 by means of a syringe-catheter arrangement 60 or the like. Preferably, bolus 56 is injected into an antecubital vein 62 and flows from there through aortic artery 44 into carotid arteries 42 and 46. Test bolus 56 usefully comprises a gadolinium chelate, such as gadopentetate dimeglumine, with a vial concentration of 0.5 mmol/mL. Bolus 56 is initially positioned at injection site 58, ready to be injected, with a quantity of normal saline behind it. At a specified point in time, pressure is applied to the saline so that bolus 56 is pushed into the vein 62. Thus, the time at which bolus 56 enters the blood stream at a particular location, for passage to the carotid arteries, is precisely known.

Figure 3:
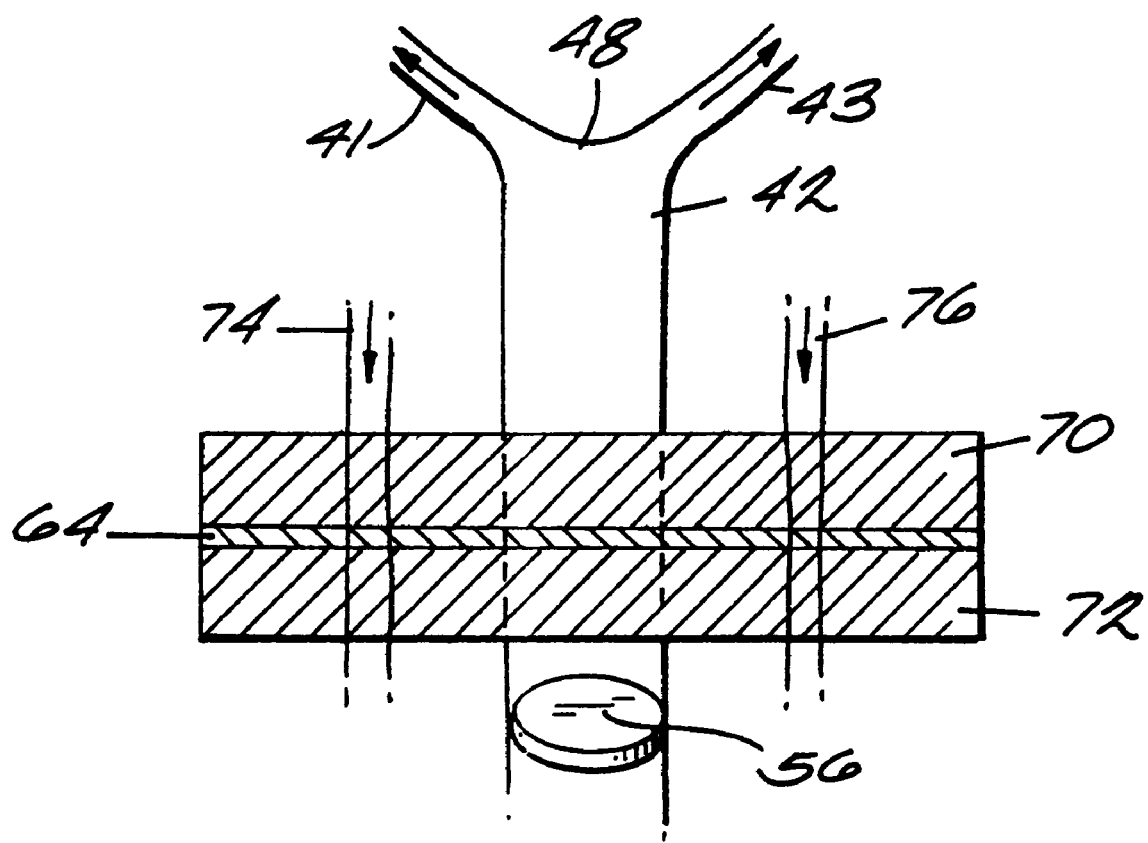
FIG. 3 shows a portion of FIG. 2 in greater detail for illustrating an embodiment of the invention.

Simultaneously, i.e., coincident in time with the injection of test bolus 56, MR system 10 commences operation to repeatedly image the same axial section taken through a carotid artery, such as axial section 64 shown in FIG. 3, taken through carotid artery 42. Section 64 usefully has a thickness on the order of 20 mm, and is acquired at a level of several centimeters below bifurcation 48. Successive images of the axial section are acquired over a period of approximately one minute, with one image being acquired approximately every second. Thus, the time of each image, measured from the injection of the test bolus, is clearly known.

Figure 4:
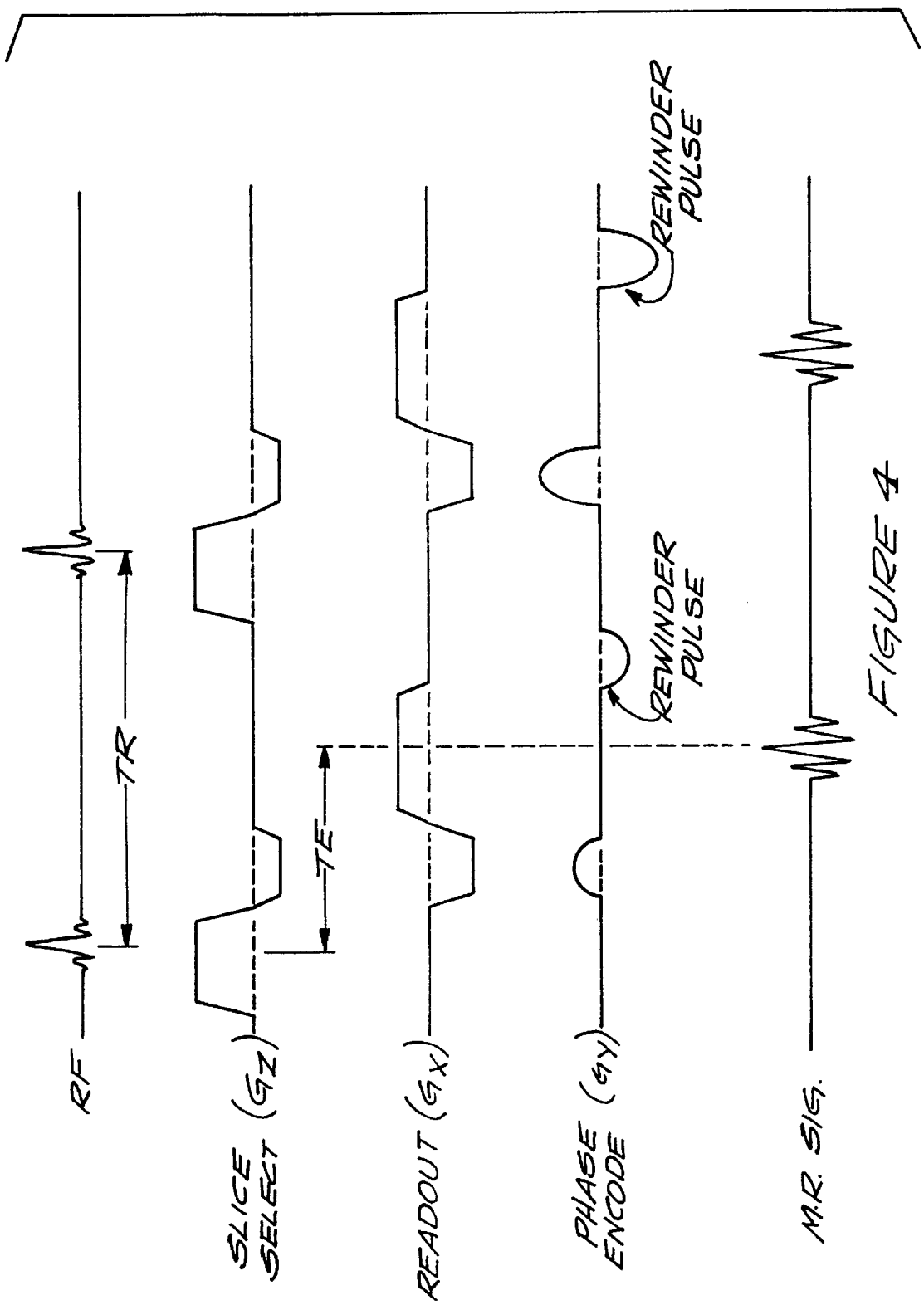
FIG. 4 is a diagram showing an MR pulse sequence for use in acquiring data for the embodiment of FIG. 3.

The basic sequence used to acquire successive images of section 64 comprises a conventional 2D fast gradient-recalled echo sequence, modified to image the same 20 mm-thick axial section repeatedly. For example, a pulse sequence known in the art as GRASS could be used, as shown in FIG. 4. Such pulse sequence may be generated by selective operation of the RF and gradient coils of MR system 10, wherein the slice select, readout and phase encoding gradient fields are produced by the Gz, Gx and Gy gradient coils, respectively. The Gy gradient is also operated to produce rewinder pulses required for the GRASS sequence. Repetition time (TR) of the sequence is usefully selected to be 17 msec, the optimum flip angle is the Ernst angle, approximately 18°, and the echo time (TE) is 2.1 msec.

Figures 5, 6:
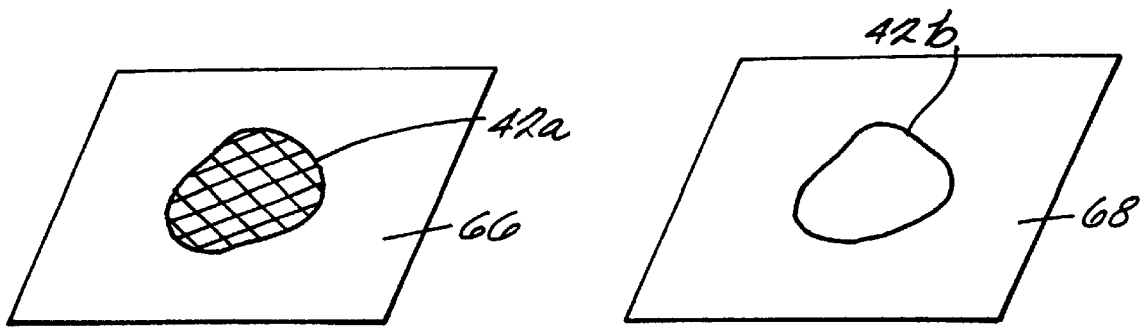
FIGS. 5 and 6 are sectional views showing images acquired at different times by means of the sequence shown in FIG. 4.

When the test bolus 56 arrives at the location of axial section 64, it produces a peak MR signal intensity which is substantially greater than the signal intensity of unenhanced blood. More particularly, for a test bolus 56 as described above, having a concentration of 0.5 mmol/mL, and for the imaging sequence likewise described above, peak signal intensity will be approximately 3.0 times the signal intensity of unenhanced blood. Thus, to detect passage of the test bolus through imaging section 64, each successive image is monitored. This is usefully accomplished by displaying respective images in real time, for viewing by an observer. For initial images of section 64 such as image 66 shown in FIG. 5, the region 42$a$, representing the portion of image 66 taken through carotid artery 42, will appear to be gray or dark. However, upon arrival of bolus 56 at axial section 64, the region 42$b$ of image 68 shown in FIG. 6, likewise representing the portion taken through carotid artery 42, will be very bright. The first image to display bright carotid region 42$b$ in the succession of acquired images is carefully noted. The time at which such image occurs, following injection of bolus 56 at site 58, indicates the transit time required for test bolus 56 to travel to the carotid arteries, and further indicates onset of carotid artery enhancement.

Referring further to FIG. 3, there are shown saturation zones 70 and 72 located immediately above and below imaging section 64, respectively, as viewed in FIG. 3. Each of the zones 70 and 72 has a thickness on the order of 80 mm, and both are in abutting relationship with section 64 so that there is no gap or spacing therebetween. Saturation zones 70 and 72 are created by applying RF excitation pulses to the spatial regions respectively comprising zones 70 and 72, as the fast acquisition sequence described above is being applied to imaging section 64. The excitation pulses have a selected low flip angle, and result in a steady state situation that effectively saturates unenhanced arterial and venous signal. That is, if MR signal is present in unenhanced blood moving upward through common carotid artery 42, such MR signal will be effectively suppressed by the steady state condition in saturation zone 72, before reaching imaging section 64. In like manner, any MR signal in unenhanced blood moving downward through veins or arteries which traverse imaging section 64, such as jugular veins 74 and 76, will be suppressed by the steady state condition in saturation zone 70. Thus, saturation zones 70 and 72 provide negligible or dark MR signal intensity for unenhanced blood which flows toward imaging section 64, from either direction.

In a useful arrangement, the RF excitation pulses which establish saturation zones 70 and 72 have the same low flip angle and repetition time, i.e. 18° and 17 msec, respectively, as the imaging sequence described above in connection with FIG. 4. Assuming saturation occurs after five excitation pulses, use of 80-mm-thick saturation zones allows saturation of any MR signal traveling at a rate of up to 80 mm in 5×17 msec (that is, at a rate of 94 cm/sec) in the common carotid arteries or in the jugular veins. The mean velocity of blood usually seen in healthy carotid arteries is about 95 cm/sec, and stenosis tends to reduce blood velocity of blood within the common carotid arteries. Thus, saturation zones of 80 mm are of an adequate thickness.

By providing saturation zones 70 and 72, the arrival of blood enhanced by test bolus 56, at imaging section 64, is clearly delineated. Such arrival further indicates the onset of carotid artery enhancement. Moreover, because saturation zones immediately adjacent to the imaging section are used in the test bolus examination, such examination is relatively insensitive to flow, and avoids large pulsatility artifacts that may occur without the use of saturation zones.

After determining the transit time of test bolus 56, between injection site 58 and the imaging site at section 64, imaging of first-pass arterial enhancement of the carotid arteries may be carried out. A full bolus (not shown) is first injected at site 58. The full bolus comprises a dose of the same contrast material used for test bolus 56, but with at least 20 times greater volume. After a delay time following injection which is equal to the transit time calculated for test bolus 56, imaging of the carotid arteries, now enhanced by arrival of the full bolus, is commenced. A conventional 3D MR angiography sequence is usefully employed for data acquisition, and useful imaging parameters include a flip angle of 30°, a repetition time of 15.6 msec, and an echo time of 3.0 msec. However, as stated above, the optimal time window after onset of carotid enhancement is only 10 seconds or less. It is very desirable to collect as much lower order k-space data during this period as possible, since such data is most significant in image reconstruction. Thus, it is useful to employ a technique known in the art as centric view ordering. In accordance therewith, beginning with the onset of the optimal time window, successive views are acquired in a monotonic, ascending order of radial distance from the k-space origin. Such technique is described, for example, in an article by Wilman and Riederer entitled "Improved Centric Phase Encoding Orders for Three-Dimensional Magnetization-Prepared MR Angiography", Magn. Reson. Med. (1996); 36:384–392.

In a modification of the invention, test bolus 56 would not be used. Instead, the full bolus, as described above, would initially be injected at the site 58. Coincident therewith, successive images of axial section 64 would be rapidly acquired and monitored, as likewise described above, and saturation zones 70 and 72 would be generated. Upon detecting arrival of the full bolus at section 64, 3D MR imaging of the carotid arteries would commence.

Figure 7:
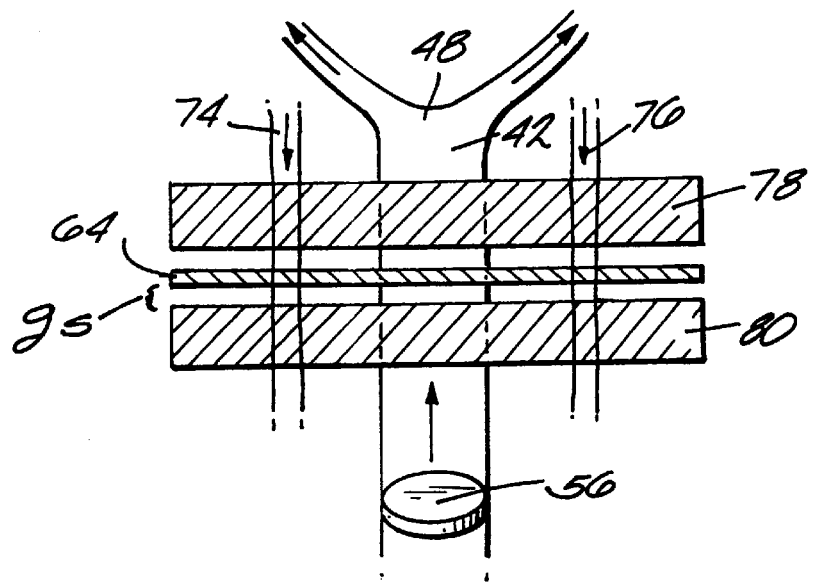
FIG. 7 shows a portion of FIG. 2 in greater detail for illustrating a further embodiment of the invention.

Referring to FIG. 7, there is shown a further modification of the invention. In such modification, the flip angle and the position of the saturation zones are altered from the arrangement described above in connection with FIG. 3. More specifically, 80 mm thick saturation zones 78 and 80 are respectively spaced apart from imaging section 64, so that there is a spatial gap $g_s$ of 30 mm between each zone and the imaging section. The flip angle in the imaging section is set to 30°. As a result, MR signal moving through either of the saturation zones 78 or 80 is fully saturated, and is then allowed to recover as it passes through the 30 mm gap. Since signal from test bolus-enhanced blood recovers more quickly during such passage then MR signal from unenhanced blood, the test bolus is clearly detected during its passage through section 64. This approach provides better suppression of signal from unenhanced blood, but is subject to more signal variation due to flow effect.

Obviously, many other modifications and variations of the present invention are possible in light of the above teachings. It is therefore to be understood that within the scope of the disclosed concept, the invention may be practiced otherwise than as specifically described.

What is claimed is:

1. A method for determining arrival time of selected contrast material at a site of MR imaging, after injection at an injection site and movement along a fluid carrying vessel, said method comprising the steps of:

injecting said contrast material into said vessel at said injection site;

coincident in time with said injection, commencing acquisition of a succession of MR images of a section taken through said vessel proximate to said imaging site;

applying excitation pulses to first and second saturation zones to selectively saturate MR signals passing therethrough, said first and second saturation zones both being positioned in proximate relationship with said section on opposing sides thereof and respectively extending away therefrom along said vessel; and monitoring respective MR images of said section to determine the time between said contrast material injection, and acquisition of the first of said MR images to indicate arrival of said contrast material at said imaging site.

2. The method of claim 1 wherein:

each of said MR images is acquired during a selectively brief time period of approximately one second.

3. The method of claim 2 wherein:

each of said MR images is acquired by means of a two-dimensional gradient recalled echo sequence.

4. The method of claim 3 wherein:

said monitoring step comprises viewing successive MR images upon acquisition, to detect the first of said MR images to display a bright spot at a specified location, which indicates arrival of said contrast material at said imaging site.

5. The method of claim 2 wherein:

said section comprises a section taken through said vessel which is oriented in substantially perpendicular relation to the direction of fluid flow.

6. The method of claim 5 wherein:

said vessel comprises a carotid artery.

7. The method of claim 5 wherein:

said section has a thickness on the order of 20 mm.

8. The method of claim 1 wherein:

each of said saturation zones is in abutting relationship with said section; and said excitation pulses comprise a succession of RF pulses of selectively low flip angle, which are applied to said first and second saturation zones to provide a steady state MR environment therein.

9. The method of claim 8 wherein:

on the order of five successive excitation pulses are employed to establish said saturation zones, and said flip angle is on the order of 18°.

10. The method of claim 1 wherein:

each of said saturation zones is slightly spaced apart from one of said opposing sides of said section; and said excitation pulses comprise RF pulses having a flip angle on the order of 30°.

11. A method for coordinating an MR angiography scan, at a specified imaging site along a fluid carrying vessel, with arrival of contrast material at the imaging site, said method comprising the steps of:

injecting said contrast material into said vessel at a specified injection site;

coincident in time with said injection, commencing acquisition of a succession of MR images of a section taken through said vessel proximate to said imaging site;

applying excitation pulses to first and second saturation zones to selectively saturate MR signals passing therethrough, said first and second saturation zones both being positioned in proximate relationship with said imaging section, on opposing sides thereof, and respectively extending away therefrom along said vessel;

monitoring respective MR images of said imaging section to detect arrival of said contrast material at said imaging site; and commencing said MR angiography scan in specified timed relationship with said arrival of said contrast material at said imaging site.

12. The method of claim 11 wherein:

said contrast material comprises a test bolus;

said method includes the step of determining the time period between injection of said test bolus at said injection site, and arrival of said test bolus at said imaging site;

said method further includes the step of injecting a full bolus into said vessel at a selected time after arrival of said test bolus at said imaging site; and said MR angiography scan is commenced after a time delay following injection of said full bolus which is equal to said time period determined in connection with said test bolus.

13. The method of claim 11 wherein:

said contrast material comprises a full bolus; and said MR angiography scan is immediately commenced upon detecting arrival of said full bolus at said imaging site.

14. The method of claim 11 wherein:

each of said MR images is acquired during a selectively brief time period of approximately one second.

15. The method of claim 14 wherein:

each of said MR images is acquired by means of a two-dimensional gradient recalled echo sequence.

16. The method of claim 11 wherein:

said monitoring step comprises viewing successive MR images upon acquisition in order to detect the first of said MR images to display a bright spot at a specified location, thereby indicating arrival of said contrast material at said imaging site.

17. The method of claim 11 wherein:

each of said saturation zones is in abutting relationship with said imaging section; and said excitation pulses comprise a succession of RF pulses of selectively low flip angle, which are applied to said first and second saturation zones to provide a steady state MR environment therein.

18. The method of claim 11 wherein:

each of said saturation zones is slightly spaced apart from one of said opposing sides of said imaging section.

19. The method of claim 11 wherein:

said vessel comprises a carotid artery.

20. Apparatus for determining arrival time of selected contrast material along a fluid carrying vessel at a site of MR imaging after injection at an injection site, said apparatus comprising:

a device for injecting said contrast material into said vessel at said injection site;

a set of MR components disposed to commence operation simultaneously with said injection to acquire a succession of MR images of a section taken through said vessel proximate to said imaging site, and to apply excitation pulses to first and second saturation zones to selectively saturate MR signals passing therethrough, said first and second saturation zones both being positioned in proximate relationship with said section, on opposing sides thereof, and respectively extending away therefrom along said vessel; and a monitoring device for successively displaying said acquired MR images to enable detection of the first of said images to show arrival of said contrast material at said imaging site, and to thereby enable determination of the time between injection of said contrast material, and arrival thereof at said imaging site.

21. The apparatus of claim 20 wherein:

said set of MR components is disposed to acquire each of said MR images during a selectively brief time period of approximately one second.

22. The apparatus of claim 21 wherein:

said set of MR components is disposed to acquire each of said MR images by means of a two-dimensional gradient recalled echo sequence.

23. The method of claim 22 wherein:

said section comprises an axial section taken through said vessel which is oriented in substantially perpendicular relation to the direction of fluid flow.

24. The apparatus of claim 23 wherein:

each of said saturation zones is in abutting relationship with said axial section; and said excitation pulses comprise a succession of RF pulses of selectively low flip angle, which are applied to said first and second saturation zones to provide a steady state MR environment therein.

25. The appratus of claim 23 wherein:

each of said saturation zones is selectively spaced apart from one of said opposing sides of said axial section; and said excitation pulses comprise RF pulses having a flip angle on the order of 30°.

* * * * *